United States Patent [19]

Maizenberg

[11] Patent Number: 4,536,157
[45] Date of Patent: Aug. 20, 1985

[54] LEVER ACTUATED CHUCK MECHANISM FOR DENTAL HANDPIECE

[75] Inventor: Leonid I. Maizenberg, Chicago, Ill.

[73] Assignee: Sybron Corporation, Rochester, N.Y.

[21] Appl. No.: 673,863

[22] Filed: Nov. 21, 1984

[51] Int. Cl.³ .............................................. A61C 1/14
[52] U.S. Cl. .................................................... 433/129
[58] Field of Search ................. 433/127, 129; 179/1 F

[56] References Cited

U.S. PATENT DOCUMENTS 4,436,512  3/1984  Garcia .................................. 433/129
4,493,645  1/1985  Nakanishi ............................ 433/129

Primary Examiner—Robert Peshock
Attorney, Agent, or Firm—Robert A. Gerlach; Robert J. Bird

[57] ABSTRACT

In a dental handpiece, a drawback bur chuck actuable to open by a cam lever mounted atop the handpiece head and acting axially downward on the chuck against a spring which urges the chuck upward into clamping engagement with a bur shank when the cam lever is in its closed position. The cam lever is rotatable on the axis of the chuck to a position to suit the convenience of the user. The chuck is removable for cleaning and positive means are provided to prevent over travel of the chuck to thereby prevent its permanent deformation.

8 Claims, 6 Drawing Figures

LEVER ACTUATED CHUCK MECHANISM FOR DENTAL HANDPIECE

BACKGROUND OF THE INVENTION

Chucks which are commonly used in high speed dental handpieces for releasably holding dental burs in place are generally of the collet type (either pushout or drawback collets) or the spring grip type. In either case, a separate tool such as a wrench or push rod is usually required to open, close, or tighten the chuck. The necessity for such a separate tool can be inconvenient and it will be readily appreciated that a chuck that does not require such a tool will be advantageous.

A wrenchless chuck mechanism is disclosed in Austrian Pat. No. 354,612. The mechanism includes a drawback collet axially movable within the head of a dental handpiece. Forward axial movement to open the collet is effected by direct downward force exerted against the top of the head, which force is transmitted to the collet forcing it axially downward against the return force of a surrounding coil spring. When such external force is removed, the spring pushes the collet back to its closed position securing a bur shank within its sidewalls. The force required to open this collet is not insignificant; in practice it is usually applied by turning the handpiece over and pushing the top of the head downward against a surface such as a table top. This can be damaging to the instrument as well as inconvenient to the user.

German Offenlegungsschrift No. DE 3129286 discloses other forms of wrenchless collet chucks. In one embodiment (see FIG. 2) the top of the head is rotatable through a nearly 360° arc to open and close a drawback collet. In another embodiment (FIG. 11) the top of the head is slidable in forward-reverse directions perpendicular to the axis of the collet, thus actuating a ball and cam combination to effect axial movement of the collet against a return spring. In addition, the German publication discloses other embodiments which operate by directly applied force without mechanical advantage essentially similar to the operation of the device shown in the Austrian patent.

SUMMARY OF THE INVENTION

It is an object of the present invention to provide a chuck mechanism for a dental handpiece which is operable without the need of a separate tool and which provides mechanical advantage so as to be operable with relatively small forces applied by the fingers of the user.

The present inventon is practiced in one form by a handpiece having a head in which a drawback collet chuck is axially mounted. The chuck is urged in a closed position, to secure a bur shank within its jaws, by a return spring. The chuck is axially movable to its open position by the movement of a cam lever mounted on top of the head and acting on the top end of the chuck. The lever is easily actuable by hand, and can be left open while a bur is being changed. The lever is also rotatable about the axis of the handpiece head to a position most suitable to the user. The chuck is removable for maintenance, and positive means are provided to prevent its damage by over-compression.

DRAWING

DESCRIPTION

Figure 1:
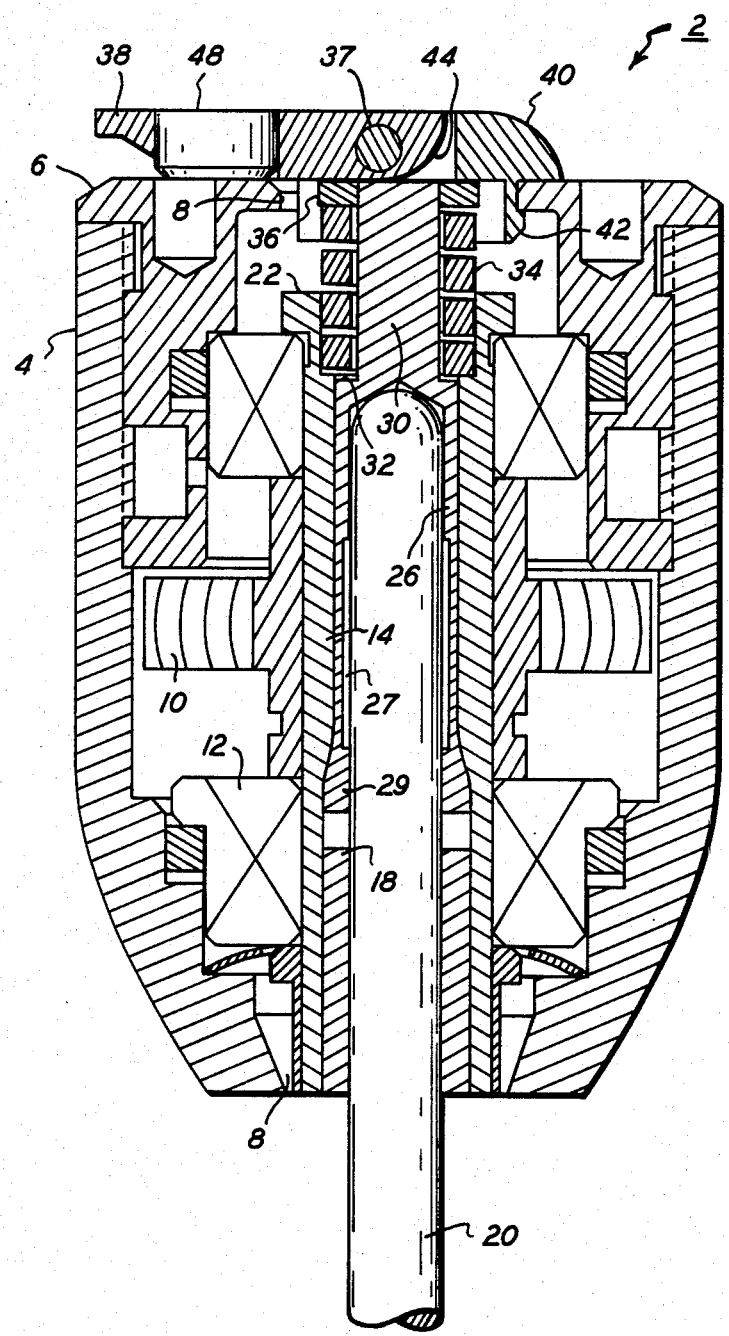
FIG. 1 is a side sectional view of the head of a dental handpiece incorporating the present invention.

Referring to FIG. 1, the head portion of a dental handpiece is generally indicated at 2 and includes a housing 4 into which a cap 6 is threaded. Housing 4 and cap 6 together form an internal cavity which is open at top and bottom axial apertures 8. An air turbine 10 is rotatably mounted in bearings 12 which are in turn mounted within the housing and cap, all of which is well known in the art.

Figure 2:
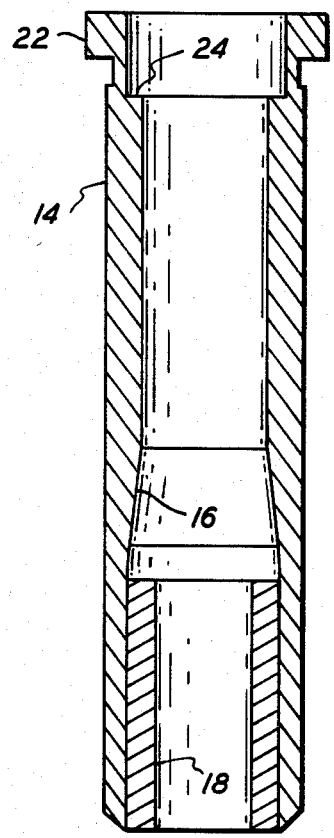
FIG. 2 is a sectional view of a bur tube which is one of the components of FIG. 1.

A flanged cylindrical bur tube or rotor tube 14 (see also FIG. 2) is fixed to the turbine rotor 10 and is rotatably mounted wihin the bearings 12. Bur tube 14 has an inner bore of a first diameter at its upper portion and a second larger diameter at its lower portion, with a tapered ramp 16 extending from one portion to the other. A bushing 18 is tightly fit within the lower bore of the bur tube 14 as an integral part therof. Bushing 18 has an inner bore of a pilot diameter in which the shank 20 of a dental bur fits closely but slidably. The upper portion of bur tube 14 includes an external flange 22 which positively engages the inner race of bearings 12, and an internal circumferential shoulder 24.

Figure 3:
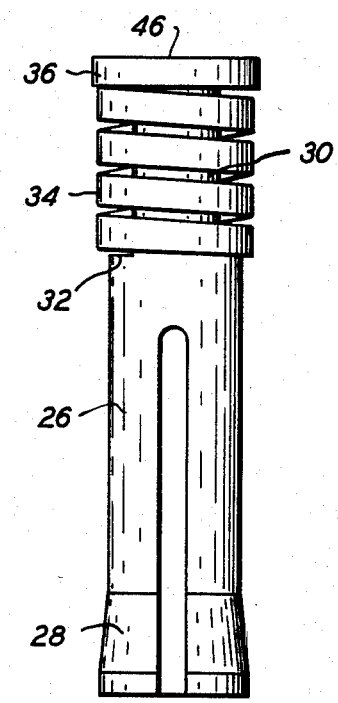
FIG. 3 is an elevation view of a chuck subassembly which is also included in FIG. 1.

A drawback chuck 26 (see also FIG. 3) is positioned within and axiably movable relative to the bur tube 14. Chuck 26 has a tapered outer surface 28 which coacts with the inner ramp 16 of the bur tube to open and close the chuck as it is moved downward or upward relative to the bur tube 14. The inner wall of the chuck is undercut along part of its length as at 27 to provide better clamping at its jaws 29. Chuck 26 includes an upstanding neck portion 30 of a smaller diameter than the main body portion of the chuck, and a shoulder 32 at the bottom of neck portion 30. A compression spring 34 surrounds the neck 30 and is held in place between shoulder 32 and a retaining ring 36 fixed around the top of the neck 30. Spring 34 bears against internal shoulder 24 of the bur tube 14 in the assembled device of FIG. 1.

In FIG. 1, in the relative positions of chuck 26 and bur tube 14 that are shown there, the spring 34 is in compression between the internal shoulder 24 (of the axially immovable bur tube 14) and the retaining ring 36 (of the axially movable chuck 26), urging the chuck upward in its clamping position against the bur shank 20. From the position shown in FIG. 1, a downward displacement of the chuck 26, against the compression spring 34 and relative to bur tube 14, opens the chuck to release the bur shank 20.

My preferred means to move the chuck to its open position against the compression spring is a cam lever 38 which is pivotally mounted by means of a pin 37 within holes 39 on a lever housing 40 which in turn is mounted atop the cap 6. Lever housing 40 includes a depending resilient flange 42 which extends partially around the inner circumference of the top opening 8 of the cap 6.

Figure 6:
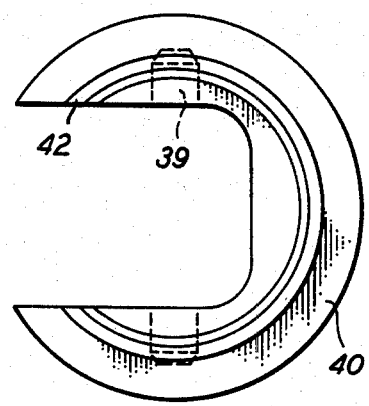
FIG. 6 is a bottom view of the lever housing of FIG. 1.

Flange 42 is resilient, due to its being less than 360° around the inner opening 8, permitting it to snap into place on the cap 6. FIG. 6 shows the C-shaped configuration of housing 40 and flange 42 which permits this resilient snap engagement within the cap opening. Cam lever 38 includes a cam surface 44 which, when lever 38 is raised, bears on the top end face 46 of the chuck retaining ring 36 and moves it downward. Lever 38 includes a magnet 48 to hold the lever in a fixed closed position on cap 6 when it is not in use.

The snap fit of the lever housing 40 on cap 6 permits housing 40 to be rotated on the cap in order to orient the cam lever 38 in a position most convenient to the user. The lever housing 40 is not loose or freely rotatable, but rather is snugly fit and rotatable to a desired position where it will remain unless moved intentionally.

In order to prevent contact between the high-speed rotating chuck retaining ring 36 and the stationary cam lever 38, a small clearance is provided between the retaining ring and the cam lever when the cam lever is in its down position. This is the result of careful dimensioning and tolerancing of a number of elements, including shank 20, jaws 29, taper 28, and so on.

An advantage of the present combination of cam lever and chuck vis a vis the prior art, in addition to the mechanical advantage it affords, is that it can be left in its raised position (at which the chuck is open) where it will remain without being held, while the user removes a bur, selects another one, and so on.

Another feature of this invention (FIG. 1) relates to its maintenance. Over some period of time and use, it is possible that oil, bacteria, or chip particles may enter and lodge within the mechanism. Removal of the chuck for periodic cleaning is achieved by simply removing the snap-on lever housing 40 and pulling the retaining ring 36 with spring 34 and chuck 26 (in other words, the entire subassembly of FIG. 3) up and out of the bur tube 14. This involves only a momentary compression of the jaws 29 while the chuck is being removed, not enough to cause permanent deformation. In order to reinsert the chuck into the bur tube, jaws 29 are easily compressed by forceps adapted for this purpose with arcuate tips to partially encircle the lower end of chuck 26, whereupon the chuck is inserted at the top of bur tube 14 and pushed into place.

A positive means is provided to prevent the jaws of the chuck from being compressed too tightly for too long, and thus taking a permanent set if, for example, the lever housing 40 were removed and the chuck left in place. In this event, the shoulder 32 of the chuck abuts the bottom of the compression spring 34, thus limiting the extent of the upward displacement of the retaining ring 36 and the chuck within the bur tube.

Figure 4:
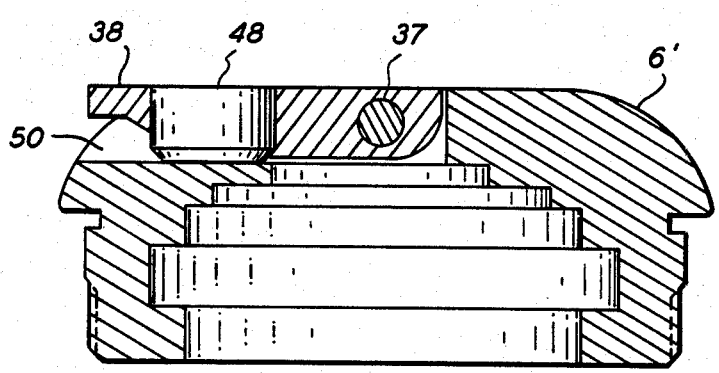
FIG. 4 is a sectional view of a cap in an alternative embodiment of this invention.
Figure 5:
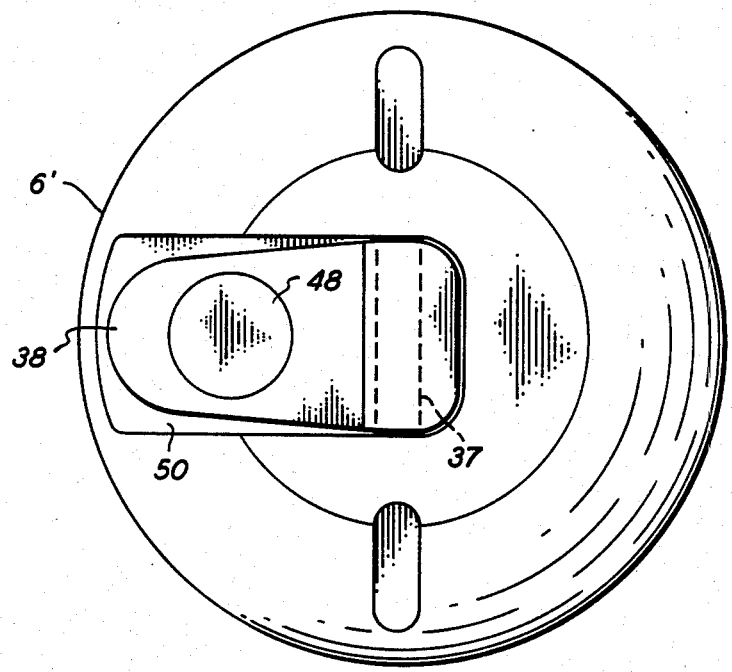
FIG. 5 is a top view of the cap of FIG. 4.

FIGS. 4 and 5 show another configuration of the cap and cam lever of this invention. In this arrangement, cam lever 38 is directly housed in the cap 6' (as distinguished from the arrangement of FIG. 1 in which a lever housing 40 is mounted on top of the cap 6) and seats in a recess 50 in the cap. In this arrangement, the cam lever 38 is not rotatable about the axis of the cap, but the overall height of the handpiece head is reduced by the absence of the separate lever housing 40 of FIG. 1. While this is a more compact arrangement, the rotatable cam lever of FIG. 1 is presently preferred.

What is claimed is:

1. A chucking mechanism for inclusion in the head of a dental handpiece, said chucking mechanism including a bur tube disposed for rotation within said head, said bur tube having a tapered inner surface along a portion of its length, a drawback chuck disposed within said bur tube for rotation therewith and having a tapered outer surface along a portion of its length to coact with the tapered inner surface of said bur tube, said chuck including a radially extending retaining ring at its top end and a spring operatively disposed between said bur tube and said retaining ring urging said chuck to a clamping position, wherein the improvement comprises:

a cam lever pivotally mounted relative to said head in operative relationship with the top end of said chuck, said cam lever being reciprocable to an open position to move said chuck to its open position against said spring and to a closed position to return said chuck to its clamping position under the influence of said spring.

2. A chucking mechanism as defined in claim 1 in which said cam lever is rotatably movable about the axis of said head to an orientation relative to said handpiece to suit the convenience of the user.

3. A chucking mechanism as defined in claim 1 wherein said cam lever is mounted on a lever housing which in turn is mounted on said head and rotatable relative to the axis of said head for positioning of said cam lever as desired by the user.

4. A chucking mechanism as defined in claim 3 in which said lever housing is removably snap-fit into said head, and said chuck is axially removable from said bur tube.

5. A chucking mechanism as defined in claim 1 in which said cam lever is recessed within said head so as to be generally flush with the top thereof.

6. A chucking mechanism as defined in claim 1 further including safety means to hold said cam lever in its closed position.

7. A chucking mechanism as defined in claim 6 in which said safety means is a magnet mounted in said cam lever for engagement with said head.

8. A chucking mechanism as defined in claim 1 further including a shoulder on said chuck to abut the bottom of said compression spring to positively limit the upward displacement of said chuck relative to said bur tube.

* * * * *